(12) United States Patent
Nour et al.

(10) Patent No.: US 9,480,535 B2
(45) Date of Patent: Nov. 1, 2016

(54) MAGNETIC RESONANCE IMAGING (MRI) GUIDED ABLATION

(75) Inventors: Sherif G. Nour, Highland Heights, OH (US); Jeffrey L. Duerk, Avon Lake, OH (US); Jamal J. Derakhshan, Cleveland Heights, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 920 days.

(21) Appl. No.: 12/423,932

(22) Filed: Apr. 15, 2009

(65) Prior Publication Data

US 2009/0264730 A1 Oct. 22, 2009

Related U.S. Application Data

(60) Provisional application No. 61/124,747, filed on Apr. 18, 2008.

(51) Int. Cl.
*A61B 5/05* (2006.01)
*A61B 18/20* (2006.01)

(52) U.S. Cl.
CPC .......... *A61B 90/37* (2016.02); *A61B 18/20* (2013.01); *A61B 2090/374* (2016.02)

(58) Field of Classification Search
USPC ................. 600/407, 408, 410–423, 424; 324/306–309, 318–322
See application file for complete search history.

(56) References Cited

U.S. PATENT DOCUMENTS

| | | | |
|---|---|---|---|
| 5,304,173 A * | 4/1994 | Kittrell et al. | 606/15 |
| 5,820,580 A * | 10/1998 | Edwards et al. | 604/22 |
| 6,126,657 A * | 10/2000 | Edwards et al. | 606/45 |
| 6,152,143 A * | 11/2000 | Edwards | 128/898 |
| 6,413,254 B1 * | 7/2002 | Hissong et al. | 606/27 |
| 7,022,117 B1 * | 4/2006 | Hohla et al. | 606/10 |
| 7,480,527 B2 * | 1/2009 | Deshpande et al. | 600/413 |
| 7,514,927 B2 * | 4/2009 | Herzka et al. | 324/318 |
| 7,539,528 B2 * | 5/2009 | Xiong et al. | 600/411 |

(Continued)

OTHER PUBLICATIONS

Lardo et al. ("Visulization and Temporal/Spatial Characterization of Cardiac Radiogrequency Ablation Lesions Using Magnetic Resonance Imaging"; American Heart Association; Mar. 16, 2000).*

(Continued)

*Primary Examiner* — Amanda Lauritzen Moher
*Assistant Examiner* — Shahdeep Mohammed
(74) *Attorney, Agent, or Firm* — Quarles & Brady LLP (57) ABSTRACT

Systems, methods, and other embodiments associated with tracking an ablative device and monitoring an ablation produced by the ablative device are described. One example method includes acquiring a magnetic resonance (MR) image of an ablative device inserted in a body and selectively controlling positioning of the ablative device based, at least in part on the MR image. The MR image may be continuously provided in real-time by an interventional MR imaging apparatus programmed to image using a tri-orthogonal plane sequence. The method may also include acquiring an MR image of an ablation performed by the ablative device, and selectively controlling the ablative device based, at least in part, on the MR image. The MR image may also be provided by the IMRI apparatus operating according to a tri-orthogonal plane sequence. In one example, the ablation may treat hypopharyngeal obstructive sleep apnea by reducing tongue base volume.

2 Claims, 7 Drawing Sheets

(56) References Cited

U.S. PATENT DOCUMENTS

| | | | |
|---|---|---|---|
| 7,727,512 B2* | 6/2010 | Lanza et al. | 424/9.361 |
| 7,844,319 B2* | 11/2010 | Susil et al. | 600/411 |
| 2001/0051783 A1* | 12/2001 | Edwards et al. | 604/22 |
| 2005/0085717 A1* | 4/2005 | Shahidi | 600/424 |
| 2005/0244036 A1* | 11/2005 | Rusinek et al. | 382/120 |
| 2008/0188947 A1* | 8/2008 | Sanders | 623/23.72 |
| 2010/0036378 A1* | 2/2010 | Savery et al. | 606/42 |

OTHER PUBLICATIONS

Lewin et al. ("Interactive MRI-guided Radiofrequency Interstitial Thermal Ablation of Abdominal Tumors:Clinical Trial for Evaluation of Safety and Feasibility"; ISMRM, 1998).*

* cited by examiner

MAGNETIC RESONANCE IMAGING (MRI) GUIDED ABLATION

PRIORITY CLAIM

This application claims the benefit of U.S. Provisional Application 61/124,747 filed Apr. 18, 2008, titled Magnetic Resonance Imaging (MRI) Guided Ablation, by the same inventors.

BACKGROUND

Macroglossia is a condition where a patient has an enlarged tongue. The enlarged tongue may contribute to hypopharyngeal obstructive sleep apnea (OSA). Reducing tongue base may help mitigate hypopharyngeal obstructive sleep apnea associated with macroglossia. Therefore conventional techniques for reducing tongue base developed over time. These conventional techniques for reducing tongue base included manual surgical resection, unguided ablation, and so on. Unguided ablations have conventionally been performed using a transoral approach. Since these approaches may have been unguided, undesirable results may have occurred. For example, ablations may have occurred in undesired areas, ablations may not have removed a desired amount of tissue, ablations may have removed too much tissue, and so on.

Ablation has been used for treating humans in a number of ways. Ablative techniques in the human body not directed at treating OSA have included radiofrequency (RF) based ablation, laser based ablation, ultrasound based ablation, and so on. These ablations have reduced tumor volume, have reduced normal tissue volume, have severed nerves, and so on. However, many of these ablations have been unguided. Those that have been guided may have been visually guided or guided by non-real time magnetic resonance (MR). Due at least in part to the limitations associated with unguided or minimally guided techniques, conventionally, only small controlled ablation zones have been created. Conventionally, ablation zone size has been limited, at least in part, due to the accuracy with which a device can be positioned, repositioned, and controlled during a procedure. Similarly, ablation zone shape has been limited, at least in part, due to the precision with which a device can be controlled. To the extent that ablations have been used to reduce tongue base, ablations have been performed in the neurovascular bundles and tongue mucosa. These ablations in the neurovascular bundles and tongue mucosa have conventionally been made under direct visual control. While useful and valuable, limitations associated with visual positioning, guidance, control, and so on, may have produced sub-optimal results. Additionally, performing ablations in the mucosa may have had undesirable results.

Previous systems for general, non-OSA treating ablations include, for example, U.S. Pat. No. 6,246,896, titled MRI guided ablation system. This type of system includes a coil in an RF, non-laser, ablation device. Previous systems also include, for example, U.S. Pat. No. 6,128,522, titled MRI-guided therapeutic unit and methods. This type of system involves ultrasound based ablation. Even lasers have been used with MRI guidance for ablation as described in *MRI-guided laser ablation of fibroids may provide alternative to hysterectomy*, by John Griffiths (Human Reproduction 2002; 17:2737-2741). However, none of these techniques describe real-time guidance to treat OSA.

BRIEF DESCRIPTION OF THE DRAWINGS

The accompanying drawings, which are incorporated in and constitute a part of the specification, illustrate various example systems, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Example systems and methods facilitate creating therapeutic-type ablations under real-time, intra-procedural, MRI guidance. The ablations may be large therapeutic-type laser ablations (LTA) having desired sizes, shapes, and so on that are designed to reduce tongue base to mitigate hypopharyngeal obstructive sleep apnea (OSA) associated with macroglossia. The therapeutic-type ablations may be created by a laser fiber ablative device. Example systems and methods may use an open-configuration interventional MR system to track, to guide, or to track and guide placement of the laser fiber. Thus, an ablative device may be more precisely positioned than may be possible under visual control or under non-real-time control. Therefore, larger, more precisely positioned and shaped ablations may be performed in single sessions, providing improvements over conventional systems in which multiple smaller ablations may be performed in multiple sessions without real-time MR control. Additionally, with precise MR control for positioning, ablation may be stopped short of the mucosa.

When an ablation is in progress, an ablation lesion may form in the tongue. Example systems and methods monitor the formation of the ablation lesion on the tongue using real-time MR imagery. For example, the location of the lesion, the size of the lesion, the rate of change of the lesion size, and so on, may be monitored. Also when an ablation is in progress, tissue may be removed by the ablation. Example systems and methods monitor tissue loss using real-time MR imagery. In one example, real-time MR imagery may provide data to an ablation control logic to facilitate controlling ablation. For example, ablation time, ablation rate, ablation device wattage, and other ablation parameters may be controlled based, at least in part, on data received from the real-time MR imaging. Thus, an ablative procedure may be more accurately monitored and controlled than may be possible under visual control or under non-real-time control.

In one example, LTAs may be created in the tongue base to reduce tongue base thickness. With real-time MR positioning and control, the LTAs may be formed in a single session. Reducing the number of sessions required to produce a desired LTA may reduce costs, may reduce patient discomfort, may reduce administrative overhead, may reduce the risk of complications, may reduce the risk of infection, may increase patient compliance, and so on.

The ablative device may be a laser. In one example, a cooled 2 cm diffusion tip Nd:YAG laser fiber with a radius of 1.5 mm may be percutaneously advanced into the tongue base. One skilled in the art will appreciate that other lasers having other properties may be employed. One skilled in the art will also appreciate that the ablative device may be a device other than a laser.

As described above, one application for MR-guided ablation is reducing tongue base to mitigate hypopharyngeal obstructive sleep apnea (OSA) associated with macroglossia. Therefore, in one example, interventional MR imaging may guide how a surgeon advances an ablative device like a laser fiber towards the midline plane between the lingual arteries. Interventional MR imaging facilitates stopping the diffusion tip laser fiber short of the surface mucosa. More generally, interventional MR imaging may guide how a surgeon advances an ablative device towards a target.

An operation may include a guidance phase and an ablation phase. In some cases, where there is a particularly large area to be ablated, or where there are multiple areas to be ablated, an operation may include multiple guidance and ablation phases. A guidance phase may include performing guidance in response to MR signals received in response to a tri-orthogonal plane sequence such as TrueFISP. In one example, the pulse sequence parameters for the TrueFISP sequence may be (TR/TE/NSA/FA; 2589 ms/5.4 ms/1/60 degrees). One skilled in the art will appreciate that other MR pulse sequences having other pulse sequence parameters may be employed.

The ablation phase may include ablation performed at a desired wattage for a desired time. During the ablation phase, the result of the ablation may be monitored using MR imaging. The MR imaging may identify the ablation size, the ablation shape, the rate of change of an ablation lesion, and so on. In one example, an evolving ablation zone may be monitored using a continuous real-time tri-orthogonal plane sequence (e.g., TrueFISP) imaging. Once again, one skilled in the art will appreciate that other MR pulse sequences may be employed.

In one example, an ablation may be planned to be performed for a pre-defined period of time (e.g., X seconds) at a pre-defined wattage (e.g., Y watts). However, as the ablation proceeds, it may be desirable to change the time period, to change the wattage, to change the time and wattage, and so on. Example systems and methods may facilitate dynamically updating the period of time, the wattage, the time and wattage, and so on for an ablation based, at least in part, on MR signals received during the ablation. In one example, a monitor logic or monitor process may receive information from continuous real-time tri-orthogonal True-FISP imaging and control ablation parameters. For example, in a first ablation, the monitor logic or monitor process may determine that an LTA is progressing at a desired rate and leave wattage and program time alone. The determination may be based, at least in part, on lesion size, lesion location, tissue temperature, and so on. However, in a second ablation, the monitor logic or monitor process may receive the information and determine that an LTA is progressing too quickly and therefore reduce program time, program wattage, or program time and wattage. While time and wattage are described, one skilled in the art will appreciate that other ablation parameters may be controlled.

Ablated regions may be created in tissues using ablation devices. The tissues may be, for example, human tissues, canine tissues, porcine tissues, equine tissues, feline tissues, and other animal tissues. In the general example, an ablation device (e.g., laser fiber) may be advanced (e.g., percutaneously, intravenously) towards a target under interventional MRI (IMRI) guidance. The IMRI imaging may guide advancing the ablation device towards the target (e.g., tumor, lypoma, heart valve, nerve branch) by providing a real-time visual indication from which a user, a logic, a user and a logic, and so on, may make advancement decisions. The IMRI imaging may include tri-orthogonal imaging that provides information from which an automated ablation control device can make ablation device positioning decisions. In addition to positioning decisions, real-time visual indicators can control an ablation process, can control an ablation device, can control an ablation process and ablation device, and so on.

The following includes definitions of selected terms employed herein. The definitions include various examples and/or forms of components that fall within the scope of a term and that may be used for implementation. The examples are not intended to be limiting. Both singular and plural forms of terms may be within the definitions.

References to "one embodiment", "an embodiment", "one example", "an example", and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable medium", as used herein, refers to a medium that stores signals, instructions and/or data. A computer-readable medium may take forms, including, but not limited to, non-volatile media, and volatile media. Non-volatile media may include, for example, optical disks, magnetic disks, and so on. Volatile media may include, for example, semiconductor memories, dynamic memory, and so on. Common forms of a computer-readable medium may include, but are not limited to, a floppy disk, a flexible disk, a hard disk, a magnetic tape, other magnetic medium, an ASIC, a CD, other optical medium, a RAM, a ROM, a memory chip or card, a memory stick, and other media from which a computer, a processor or other electronic device can read.

"Logic", as used herein, includes but is not limited to hardware, firmware, software in execution on a machine, and/or combinations of each to perform a function(s) or an action(s), and/or to cause a function or action from another logic, method, and/or system. Logic may include a software controlled microprocessor, a discrete logic (e.g., ASIC), an analog circuit, a digital circuit, a programmed logic device, a memory device containing instructions, and so on. Logic may include one or more gates, combinations of gates, or other circuit components. Where multiple logical logics are described, it may be possible to incorporate the multiple logical logics into one physical logic. Similarly, where a single logical logic is described, it may be possible to distribute that single logical logic between multiple physical logics.

An "operable connection", or a connection by which entities are "operably connected", is one in which signals, physical communications, and/or logical communications may be sent and/or received. An operable connection may include a physical interface, an electrical interface, and/or a data interface. An operable connection may include differing combinations of interfaces and/or connections sufficient to allow operable control. For example, two entities can be operably connected to communicate signals to each other directly or through one or more intermediate entities (e.g., processor, operating system, logic, software). Logical and/or physical communication channels can be used to create an operable connection.

"Signal", as used herein, includes but is not limited to, electrical signals, optical signals, analog signals, digital signals, data, computer instructions, processor instructions, messages, a bit, a bit stream, or other means that can be received, transmitted and/or detected.

"User", as used herein, includes but is not limited to one or more persons, software, computers or other devices, or combinations of these.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, determining, and so on, refer to actions and processes of a computer system, logic, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 1:
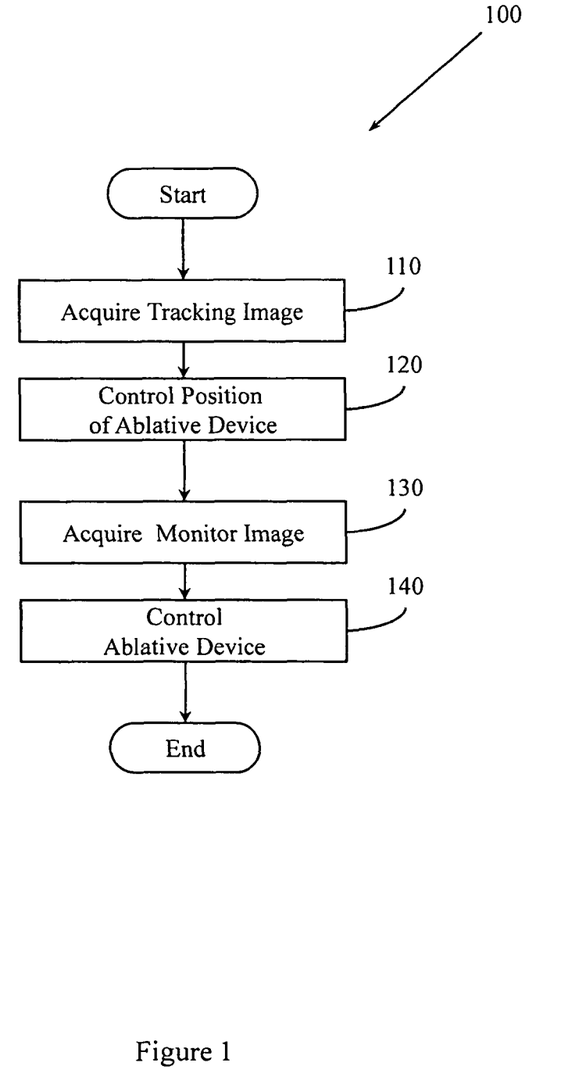
FIG. 1 illustrates an example method associated with MRI guided ablation.

FIG. 1 illustrates a method 100 associated with tracking an ablative device and monitoring an ablation performed by the ablative device. In one example, the ablative device is to produce a large therapeutic-type laser ablation (LTA). While laser ablation is described, it is to be appreciated that other ablative devices (e.g., radiofrequency, cryogenic freezing, focused ultrasound) may be employed. Method 100 may include, at 110, acquiring a first magnetic resonance (MR) image of the ablative device inserted in a body. In one example, the ablative device may be a laser fiber that has been inserted percutaneously, intravenously, and so on, into the tongue of a patient. In one example, the first MR image is acquired in response to a tri-orthogonal plane sequence (e.g., TrueFISP) pulse sequence. The first MR image may be acquired continuously in real-time while the ablative device is being moved in the body. While a TrueFISP sequence is described, it is to be appreciated that other pulse sequences may be employed.

Method 100 may also include, at 120, selectively controlling the position of the ablative device based, at least in part, on the first MR image. In different examples the ablative device may be controlled directly by a user, may be controlled indirectly by a user through a machine, may be controlled directly by a machine, and so on. For example, a surgeon may manually control the ablative device either directly or indirectly. By way of illustration, the surgeon may hold one portion of an ablative device and manually position another portion. By way of further illustration, the surgeon may work a control of a robot or other machine that is holding the ablative device. The machine may provide finer control and less impact for undesired movements (e.g., shaking, hiccup, sneeze) than possible with a surgeon's hand directly on the ablative device. By way of still further illustration, the ablative device may be part of a robot, machine, or other device, or may be held by a robot, machine, or other device. The robot, machine, or other device may be programmed to control the position of the ablative device based, at least in part, on the first MR image. For example, the machine may control the position of the ablative device as a function of image analysis.

Method 100 may also include, at 130, acquiring a second MR image of an ablation performed by the ablative device. In one example, the second MR image is acquired in response to a tri-orthogonal plane sequence (e.g., TrueFISP). Once again, while a TrueFISP sequence is described, it is to be appreciated that other pulse sequences may be employed. In one example, the second MR image is acquired continuously in real-time during the ablation.

Method 100 may also include, at 140, selectively controlling the ablative device based, at least in part, on the second MR image. In different examples the ablative device may be controlled directly by a user, indirectly by a user, automatically by a machine, and so on. For example, the surgeon may manually control the ablative device either directly or indirectly after viewing the second MR image. By way of illustration, the surgeon may hold one portion of the ablative device and manually position another portion in response to seeing the second MR image, or in response to seeing a series of second MR images. By way of further illustration, the surgeon may control a robot or other machine that is holding the ablative device to reposition or maintain the position of the ablative device in response to viewing the second MR image(s). The machine may provide hands free operation that facilitates maintaining the device in a fixed position, moving the device in desired paths at desired rates and within defined boundaries, and so on. The machine may also provide programmed patterns (e.g., circle, oval, sphere) that can be ablated after the surgeon correctly places the device. By way of still further illustration, the ablative device may be part of a robot, machine, or other device, or may be held by a robot, machine, or other device that is programmed to control the position of the ablative device based, at least in part, on the second MR image(s).

While repositioning is described, controlling the ablative device may include other actions. For example, controlling the ablative device may include controlling the wattage at which the device operates, a wavelength produced by the ablative device, an on/off sequence that controls when and whether the ablative device is ablating, and so on. For example, the first MR image and a set of second MR images may be used to position an ablative device, then a set of second MR images may be used to control turning on and off the ablative device to achieve an ablation of desired proportions. Additionally, in one example, the machine may control operating parameters of the ablative device as a function of image analysis.

While FIG. 1 illustrates various actions occurring in serial, it is to be appreciated that various actions illustrated in FIG. 1 could occur substantially in parallel. By way of illustration, a first process could acquire tracking images and control ablative device position while a second process could acquire ablation images and control ablative device operation. While two processes are described, it is to be appreciated that a greater and/or lesser number of processes could be employed and that lightweight processes, regular processes, threads, and other approaches could be employed.

Figure 2:
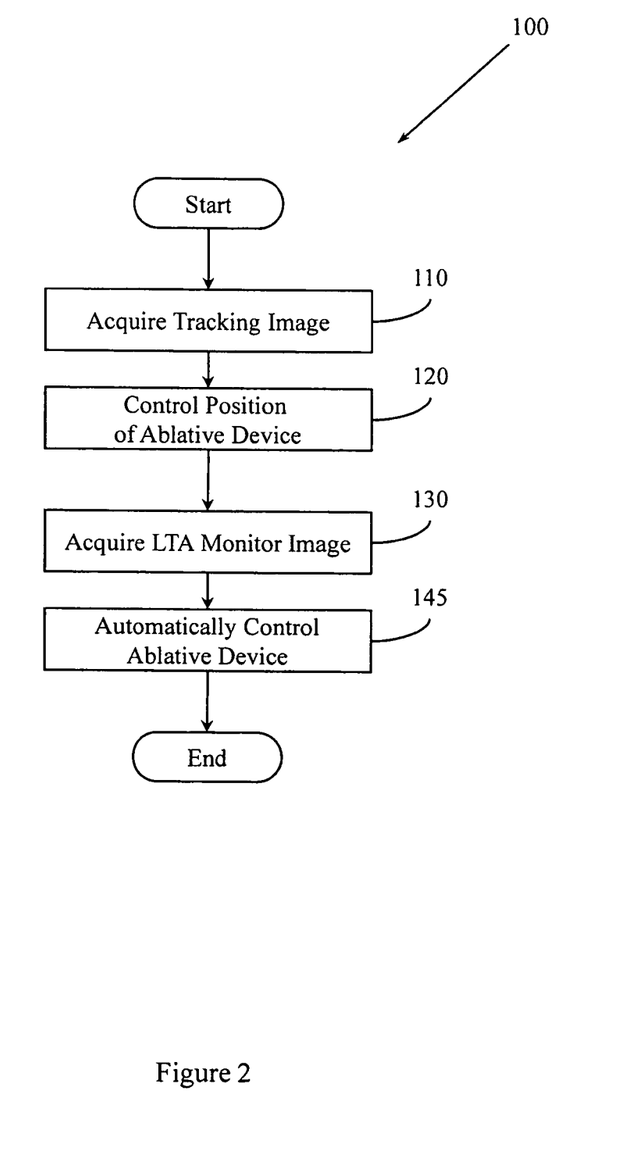
FIG. 2 illustrates an example method associated with MRI guided midline laser glossectomy to reduce tongue base.

FIG. 2 illustrates a second embodiment of method 100. In this embodiment, method 100 includes, at 145, selectively automatically controlling the ablative device based, at least in part, on the second MR image. For example, a logic may automatically track identifiable LTA parameters in the ablation images and automatically make adaptations, suggest adaptations, and so on, based on the parameters. The parameters may include, for example, LTA size, LTA shape, rate of change for LTA size, rate of change for LTA shape, and so on. The logic may track the parameters using, for example, pattern matching and/or other artificial intelligence techniques.

For example, it may be desired to produce an ablation of a certain size and a certain shape at a certain location. MR images may first be used to position the ablative device at a desired start position. An initial ablation may then be undertaken. Second MR images may be taken to see how the tissue responded to the first ablation. Some tissues may ablate at different rates than other tissues under different conditions and therefore initial ablations may be made to determine the rate at which tissue is ablating. Some ablations may proceed differently than other ablations under different conditions. Thus, rather than simply applying a fixed or predetermined amount of energy for a fixed or predetermined amount of time, a series of intra-operative images may be acquired to guide the surgeon's hand. This overcomes issues with the prior art where ablations may have been unguided.

In another example, a first portion of an ablation may be performed under first conditions (e.g., wattage) while a second portion of the ablation may be performed under second conditions. For example, a gross ablation may be undertaken to remove the first 90% of tissue to be ablated while a fine ablation may be undertaken to remove the last 10% of tissue to be ablated. The gross ablation and the fine ablation may be undertaken with different wattages. The gross ablation may be made in the center of the area to be ablated while the fine ablation may occur at the margins of the area to be ablated, around critical structure or tissue to be spared, and so on.

Figure 3:
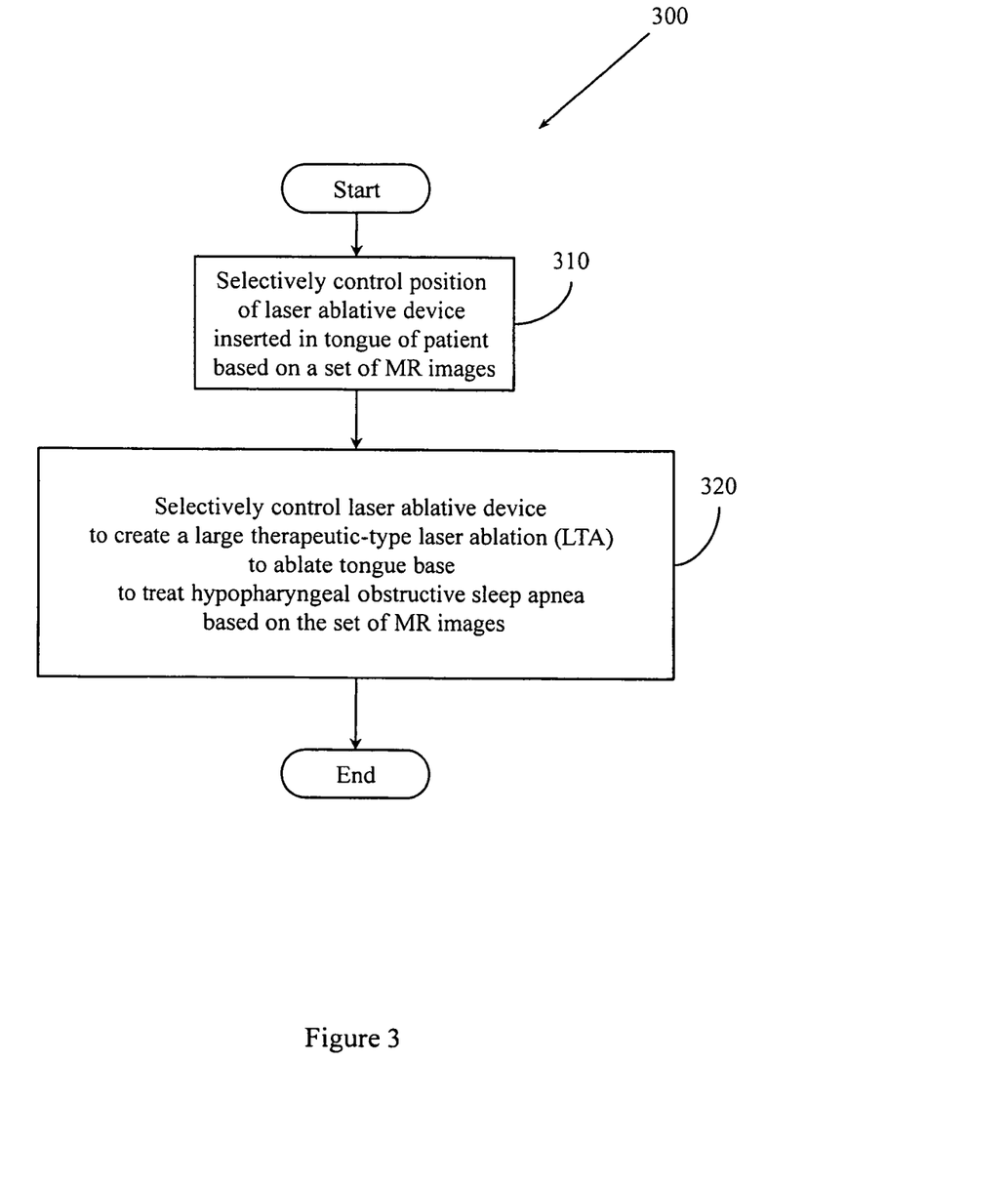
FIG. 3 illustrates an example method associated with treating hypopharyngeal obstructive sleep apnea by ablating tongue base.

FIG. 3 illustrates a method 300 associated with treating hypopharyngeal obstructive sleep apnea associated with macroglossia. Method 300 includes, at 310, selectively controlling the position of a laser ablative device inserted in the tongue of a patient based, at least in part on a set of MR images. Selectively controlling the position of the laser ablative device at 310 may include controlling an interventional MR imaging apparatus to produce the set of MR images. Selectively controlling the position of the laser ablative device at 310 may also include selectively advancing the laser ablative device towards the midline plane between the lingual arteries of the tongue based, at least in part, on the set of MR images. Selectively controlling the position of the laser ablative device at 310 may also include stopping the laser ablative device short of the surface mucosa based, at least in part, on the set of MR images.

In one example, selectively controlling the position of the laser ablative device at 310 includes controlling a machine that is configured to hold the laser ablative device and that is configured to move the laser ablative device. The machine may be, for example, a surgical device, a robot, a mechanical arm, and so on.

Method 300 also includes, at 320, selectively controlling the laser ablative device to ablate tongue base to treat hypopharyngeal obstructive sleep apnea based, at least in part, on the set of MR images. Selectively controlling the laser ablative device to ablate tongue base at 320 may include controlling the laser ablative device to create a large therapeutic-type laser ablation (LTA) having a desired size, a desired shape, and so on.

The laser ablative device may be, for example, a diffusion tip laser fiber. In one example, selectively controlling the laser ablative device at 320 includes controlling ablation parameters by controlling operating parameters of the laser ablative device as a function of an image(s) in the set of MR images. For example, operating wattage, operating time, and so on, may be controlled at 320 based on an image(s) in the set of MR images. By way of illustration, an image in the set of MR images may show that the ablation is proceeding more slowly than desired. Therefore, wattage may be increased as a function of the image.

Monitoring ablative device position and monitoring ablation is facilitated by seeing the device and the ablation in real time with accuracy sufficient to guide a surgeon. Therefore, method 300 may include controlling the interventional MR imaging apparatus to produce a tri-orthogonal plane sequence (e.g., TrueFISP) and to acquire the set of images in response to the tri-orthogonal plane sequence. In one example, method 300 may include controlling the interventional MR imaging apparatus to produce the tri-orthogonal plane sequence to have pulse sequence parameters of TR=2589 ms, TE=5.4 ms, NSA=1, and FA=60 degrees, where TR represents repetition time, TE represents echo time, NSA represents number of signal averages, and FA represents flip angle.

Figure 4:
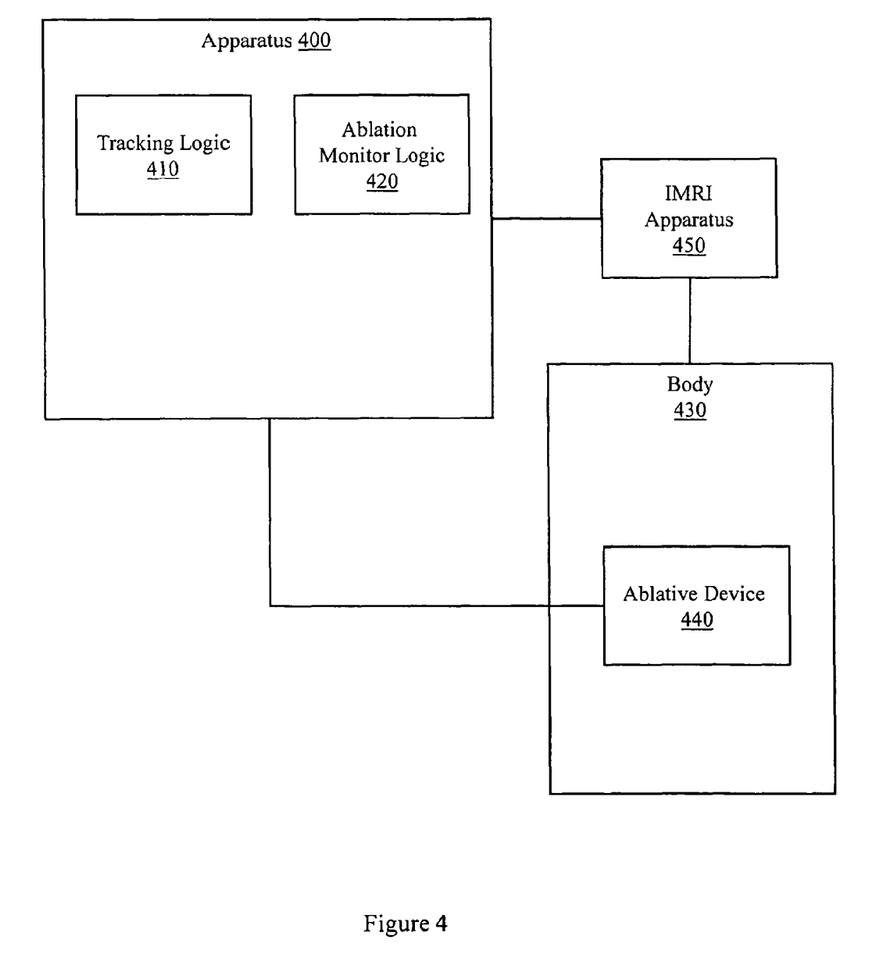
FIG. 4 illustrates an example system associated with MRI guided ablation.

FIG. 4 illustrates an apparatus 400 associated with MRI guided ablation. The ablation may be performed, for example, by laser ablation, by radiofrequency ablation, by cryogenic freezing, by focused ultrasound ablation, and so on. Apparatus 400 may include a tracking logic 410 to track an ablative device 440 inserted in a body 430. In one example, the ablative device 440 may be inserted into the tongue of a human and the ablation may be intended to reduce the volume of the tongue. While a human body and a tongue are described, it is to be appreciated that other locations (e.g., heart, kidney, brain) or other species (e.g., equine, canine, feline) may be involved.

The ablative device 440 may include, for example, a laser fiber. The tracking logic 410 may receive a continuous real-time signal from an interventional MRI apparatus 450 that is performing an MRI process on a body 430. While a continuous real-time signal is described, one skilled in the art will appreciate that a less than continuous real-time signal may produce visual results sufficient to track, guide, and control an inserted device. In one example, the interventional MRI apparatus 450 may employ a tri-orthogonal plane (e.g., TrueFISP) sequence or other suitable MR imaging method to track the ablative device 440. The tri-orthogonal plane pulse sequence facilitates providing the ablation monitor logic 420 or the tracking logic 410 with a continuous real-time signal. Thus, a real-time display of the location of the ablative device 440 may be available to, for example, a surgeon who is to position the ablative device 440 at a desired location. The real-time display may also be available to a pattern matching or image analysis logic that may provide suggestions to the surgeon or that may automatically take an action (e.g., emergency shutoff) based on the continuous real-time signal.

Apparatus 400 may also include an ablation monitor logic 420 to monitor an ablation performed in the body 430 by the ablative device 440. In one example, the ablative device 440 is to produce a large therapeutic-type laser ablation (LTA). Once again the interventional MRI apparatus 450 may employ a tri-orthogonal plane (e.g., TrueFISP) sequence to monitor the formation of the LTA.

Figure 5:
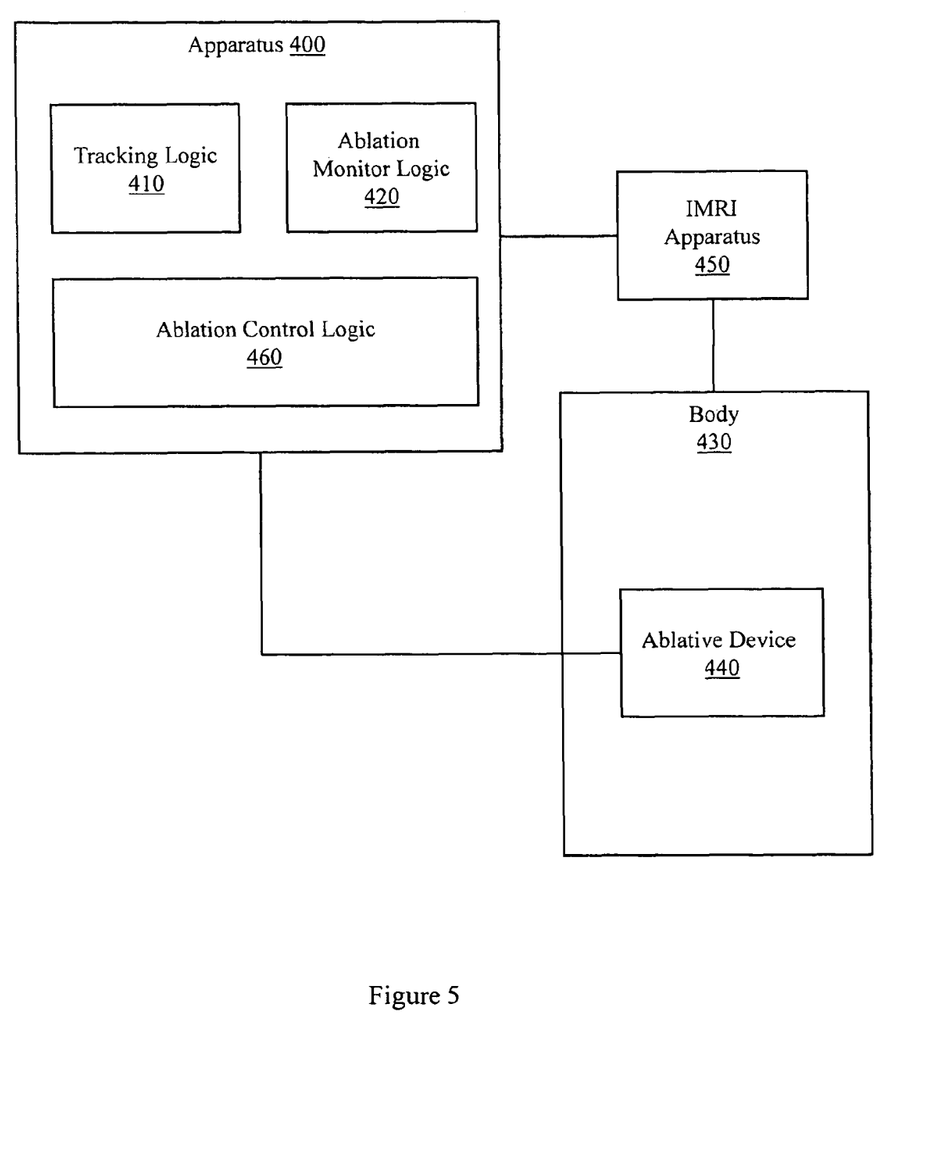
FIG. 5 illustrates an example system associated with MRI guided midline laser glossectomy to reduce tongue base.

FIG. 5 illustrates another embodiment of apparatus 400. In this embodiment, apparatus 400 includes an ablation control logic 460. Ablation control logic 460 may selectively automatically control the ablative device 440. The control may be based, at least in part, on a signal from the ablation monitor logic 420. The signal may be provided in response to image analysis, pattern matching, artificial intelligence heuristics, surgeon input, and so on. In one example, the ablation control logic 460 is to control a wattage at which the ablative device 440 operates. In one example, the ablation monitor logic 420 may provide an emergency cutoff signal when the LTA formation rate exceeds a desired threshold.

Figure 6:
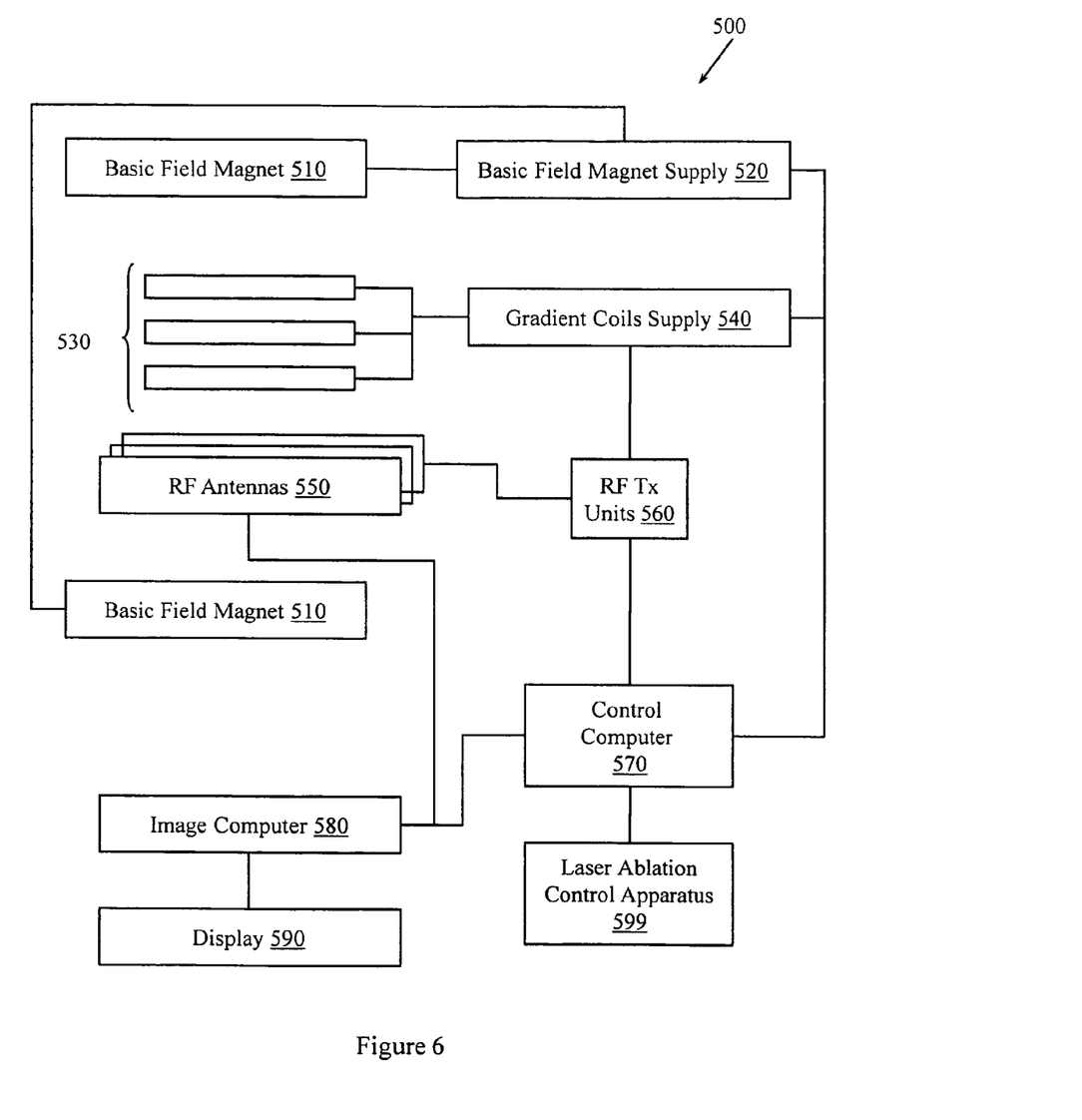
FIG. 6 illustrates an MRI apparatus associated with MRI guided ablative device tracking and ablation monitoring.

FIG. 6 illustrates an example MRI apparatus 600 configured with a laser ablation control apparatus 699 to facilitate IMRI guided laser ablation control. The laser ablation control apparatus 699 may be configured with elements of example apparatus described herein and/or may perform example methods described herein.

The apparatus 600 includes a basic field magnet(s) 610 and a basic field magnet supply 620. Ideally, the basic field magnets 610 would produce a uniform $B_0$ field. However, in practice, the $B_0$ field may not be uniform, and may vary over an object being imaged by the MRI apparatus 600. MRI apparatus 600 may include gradient coils 630 configured to emit gradient magnetic fields like $G_S$, $G_P$ and $G_R$, where $G_S$ denotes the slice select gradient, $G_P$ denotes a phase encoding gradient and $G_R$ denotes a readout gradient. The gradient coils 630 may be controlled, at least in part, by a gradient coils supply 640. In some examples, the timing, strength, and orientation of the gradient magnetic fields may be controlled, and thus selectively adapted during an MRI procedure.

MRI apparatus 600 may include a set of RF antennas 650 that are configured to generate RF pulses and to receive resulting magnetic resonance signals from an object to which the RF pulses are directed. In some examples, how the pulses are generated and how the resulting MR signals are received may be controlled and thus may be selectively adapted during an MRI procedure. Separate RF transmission and reception coils can be employed. The RF antennas 650 may be controlled, at least in part, by a set of RF transmission units 660. An RF transmission unit 660 may provide a signal to an RF antenna 650.

The gradient coils supply 640 and the RF transmission units 660 may be controlled, at least in part, by a control computer 670. In one example, the control computer 670 may be programmed to control an IMRI device as described herein. The magnetic resonance signals received from the RF antennas 650 can be employed to generate an image and thus may be subject to a transformation process like a two dimensional FFT that generates pixilated image data. The transformation can be performed by an image computer 680 or other similar processing device. The image data may then be shown on a display 690. While FIG. 6 illustrates an example MRI apparatus 600 that includes various components connected in various ways, it is to be appreciated that other MRI apparatus may include other components connected in other ways.

Figure 7:
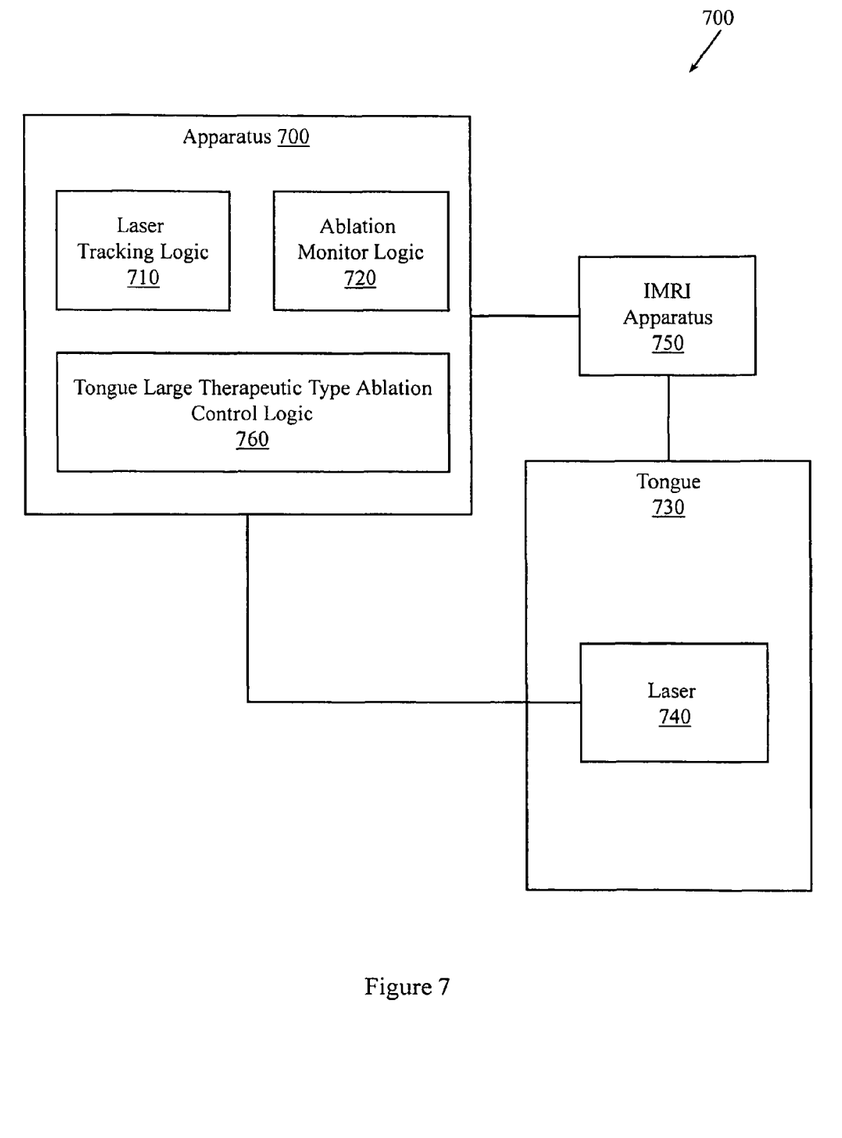
FIG. 7 illustrates an example system associated with treating hypopharyngeal obstructive sleep apnea by ablating tongue base.

FIG. 7 illustrates an apparatus 700 configured to ablate tongue base to treat hypopharyngeal obstructive sleep apnea. Apparatus 700 includes a laser tracking logic 710 configured to track a laser 740 inserted in the tongue 730 of a patient. The laser tracking logic 710 tracks the laser 740 based on a continuous real-time signal provided by an interventional MRI apparatus 750.

Apparatus 700 also includes an ablation monitor logic 720 that is configured to monitor a large therapeutic type ablation in the tongue 730 also based on the continuous real-time signal provided by the interventional MRI apparatus 750. In one example the continuous real-time signal may be presented in the form of MR images. In another example, the continuous real-time signal may be presented in the form of data describing laser position. The data may describe, for example, an actual position of a laser, a position of the laser relative to a desired location, a position of the laser relative to a reference position, and so on.

The laser tracking logic 710 is configured to control advancing the laser 740 towards the midline plane between the lingual arteries of the tongue 730 and to stop the laser 740 short of the surface mucosa. Thus, the apparatus 700 provides improved guidance over conventional systems. The improved guidance facilitates achieving greater precision in the placement of the laser 740.

The accurate guidance and positioning depends on having accurate real time images. Therefore the apparatus 700 is configured to control the interventional MRI apparatus 750 to produce a tri-orthogonal plane (e.g., TrueFISP) sequence to produce images that facilitate tracking the laser 740.

Apparatus 700 may also include a large therapeutic type ablation control logic 760 configured to selectively control the laser 740 based, at least in part, on a signal from the ablation monitor logic 720. The signal may based on an analysis of the continuous real-time signal provided by the IMRI apparatus 750. In one example, the control logic 760 is configured to control a wattage at which the laser 740 operates to ablate tongue tissue. The wattage may be pre-selected to start at an initial level but then may be varied during lesion formation. For example, a first wattage may be employed to start lesion formation, a second wattage may be employed while lesion formation is proceeding at a desired rate, and a third wattage may be employed to increase or decrease lesion formation rate. In one example, an emergency cutoff may be produced by rapidly changing the wattage to zero.

While example systems, methods, and so on have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and so on described herein. Therefore, the invention is not limited to the specific details, the representative apparatus, and illustrative examples shown and described. Thus, this application is intended to embrace alterations, modifications, and variations that fall within the scope of the appended claims.

To the extent that the term "includes" or "including" is employed in the detailed description or the claims, it is intended to be inclusive in a manner similar to the term "comprising" as that term is interpreted when employed as a transitional word in a claim.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

To the extent that the phrase "one or more of, A, B, and C" is employed herein, (e.g., a data store configured to store one or more of, A, B, and C) it is intended to convey the set of possibilities A, B, C, AB, AC, BC, and/or ABC (e.g., the data store may store only A, only B, only C, A&B, A&C, B&C, and/or A&B&C). It is not intended to require one of A, one of B, and one of C. When the applicants intend to indicate "at least one of A, at least one of B, and at least one of C", then the phrasing "at least one of A, at least one of B, and at least one of C" will be employed.

What is claimed is:

1. An apparatus for treating hypopharyngeal obstructive sleep apnea associated with macroglassia in a patient, comprising:
   a laser ablative device including a cooled 2 cm diffusion tip neodymium-doped yttrium aluminium garnet (Nd: YAG) laser fiber;
   a processor that is programmed to:
   (i) receive a continuous real-time signal produced by continuous real-time imaging performed by a magnetic resonance imaging (MRI) apparatus,
   (ii) control a position of the laser fiber ablative device inserted in the tongue of the patient as a function of the continuous real-time signal from the interventional MRI apparatus,
   where controlling the position includes advancing the laser ablative device towards a midline plane between lingual arteries of the tongue and stopping the laser ablative device short of a surface mucosa;
   (ii) monitor an ablation performed in the tongue by the laser fiber ablative device as the function of the continuous real-time signals,
   where the ablation reduces the mass of the tongue to treat hypopharyngeal obstructive sleep apnea (OSA) associated with macroglossia by forming a large therapeutic-type laser ablation in the tongue, and
   (iii) control the operation of the laser ablative device based, at least in part, on a signal, the signal being a function of an analysis of the continuous real-time signal produced by continuous real-time imaging performed by the MRI apparatus to treat hypopharyngeal obstructive sleep apnea associated with macroglassia in the patient,
   where the analysis analyzes a size of a lesion formed by the laser ablative device, a location of the lesion formed by the laser ablative device, a shape of the lesion formed by the laser ablative device, a rate of change of the size of the lesion formed by the laser ablative device, and a rate of change of the shape of the lesion formed by the laser ablative device, and
   where controlling the operation of the laser ablative device includes controlling a wattage at which the laser ablative device operates to ablate tissue or a time for which the laser ablative device operates.

2. The apparatus of claim 1, where the processor is further configured to control the interventional MRI apparatus to produce a tri-orthogonal TrueFISP pulse sequence to track the laser ablative device and where the tri-orthogonal TrueFISP pulse sequence facilitates visualizing the laser ablative device in three dimensions while inserted in the tongue.

* * * * *